United States Patent [19]

Nakada et al.

[11] Patent Number: 5,035,710
[45] Date of Patent: Jul. 30, 1991

[54] BALLOON FOR AN INTRAOCULAR LENS AND PROCESSES FOR ITS PRODUCTION

[75] Inventors: Kazuhiko Nakada; Akihiro Yasuda; Makoto Ichikawa, all of Nagoya, Japan

[73] Assignee: Menicon Co., Ltd., Nagoya, Japan

[21] Appl. No.: 308,533

[22] Filed: Feb. 10, 1989

[30] Foreign Application Priority Data

| Feb. 12, 1988 | [JP] | Japan | 63-31582 |
| Mar. 4, 1988 | [JP] | Japan | 63-52449 |

[51] Int. Cl.$^5$ ............................................. A61F 2/16
[52] U.S. Cl. ................................................ 623/6
[58] Field of Search ..................................... 623/6

[56] References Cited

U.S. PATENT DOCUMENTS

| 3,010,153 | 11/1961 | Bittner | 264/219 |
| 3,989,787 | 11/1976 | Scott, Jr. et al. | 264/114 |
| 4,373,218 | 2/1983 | Schachar | 623/6 |
| 4,377,897 | 3/1983 | Eichenbaum et al. | 29/516 |
| 4,416,837 | 11/1983 | Neefe | 264/2.1 |
| 4,449,257 | 5/1984 | Koeniger | 623/6 |
| 4,542,542 | 9/1985 | Wright | 623/6 |
| 4,573,998 | 3/1986 | Mazzocco | 623/6 |
| 4,585,457 | 4/1986 | Kalb | 623/6 |
| 4,685,921 | 8/1987 | Peyman | 623/6 |
| 4,693,717 | 9/1987 | Michelson | 623/6 |
| 4,713,072 | 12/1987 | Bowald | 623/6 |
| 4,822,360 | 4/1989 | Deacon | 623/6 |

FOREIGN PATENT DOCUMENTS

| 0134363 | 3/1985 | European Pat. Off. . |
| 286270 | 10/1952 | Switzerland . |
| WO84/0129 | 4/1984 | |

Primary Examiner—Ronald Frinks
Attorney, Agent, or Firm—Oblon, Spivak, McClelland, Maier & Neustadt

[57] ABSTRACT

A balloon for an intraocular lens, which is a unitary elastic hollow body made of an elastomer and having a convex lenticular shape without projections along its circumference, which gives, when inserted in a lens capsule, a configuration corresponding substantially to the shape of the lens capsule, said hollow body having a wall thickness of from 0.001 to 0.1 mm at its optical portion and a diameter of from 6 to 13 mm, and capable of being inflated in the lens capsule to form an intraocular lens when a light transmitting injection material is injected into the hollow body.

4 Claims, 9 Drawing Sheets

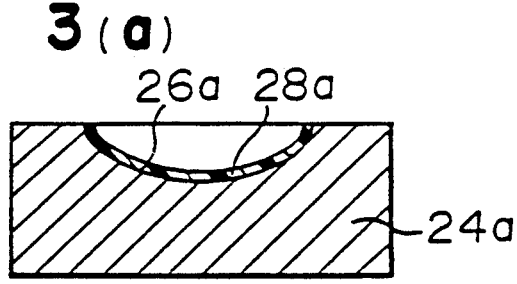
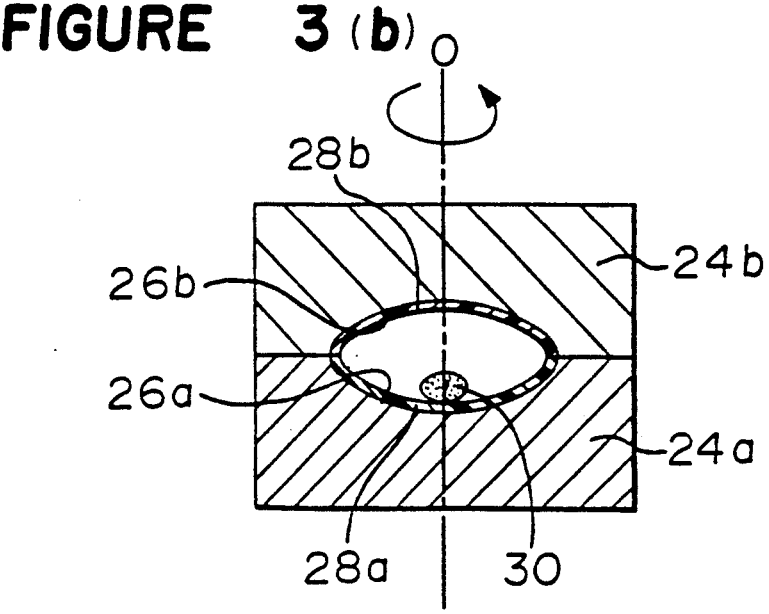
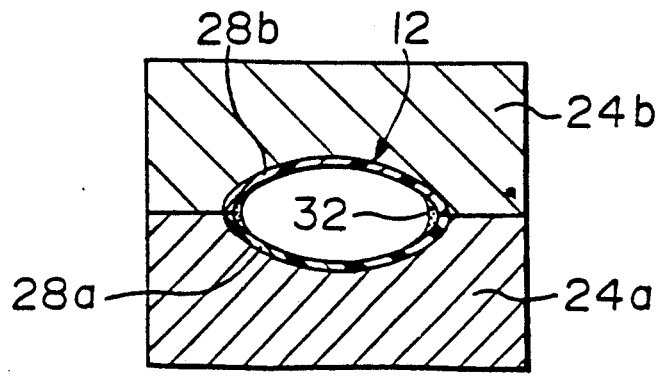

BALLOON FOR AN INTRAOCULAR LENS AND PROCESSES FOR ITS PRODUCTION

The present invention relates to a balloon for an intraocular lens and processes for its production. More particularly, it relates to a balloon useful as an intraocular lens to be used as a lens for correcting the eyesight or vision after the surgery to remove a cataract and capable of being inserted through a small incision and being snugly fit and held in a lens capsule, and advantageous processes for its production.

With respect to intraocular lenses useful as lenses for correcting the eyesight or vision after the surgery to remove cataracts, there has been an increase in their use under a number of clinical tests along with improvements of the lenses and progress of the surgical techniques in recent years It has been recognized that they are functionally far superior to eye glasses or contact lenses for aphakias, which used to be commonly employed.

Such intraocular lenses are generally classified into anterior chamber lenses, iris-supported lenses and posterior chamber lenses depending upon the sites for implantation. Among them, a posterior chamber lens implanted at the position for the crystalline lens is preferred. It is particularly preferred to implant it in the capsule of the posterior chamber, since such is most natural.

To implant such an intraocular lens in the lens capsule, it is necessary to incise the sclera of the eye for the insertion of the lens into the capsule, and such an incision is required to be sufficiently large for the insertion of the lens therethrough. However, if the incision is large, astigmatism is likely to result after the surgery. Accordingly, it is desired that an intraocular lens to be inserted is capable of being inserted through a small incision.

For this purpose, some proposals have been made for intraocular lenses to be inserted and fixed in lens capsules. For example, U.S. Pat. No. 4,449,257 proposes to use a swellable lens made of a water-absorptive hydroxyethyl methacrylate polymer and to insert it in a small dried state and let it expand with the uptake of aqueous humor in the eye to form a soft lens. However, with an intraocular lens of such a structure, the incision of the sclera can not be reduced beyond a level of about 4 mm when it is made of a hydroxyethyl methacrylate polymer, although it depends on the swellability of the material.

Further, since an intraocular lens is to be implanted in the lens capsule for a crystalline lens, it is required to have elasticity to follow the movememt of the crystalline lens. It is further desired to have the same shape as the crystalline lens and to be capable of being intimately fit in the lens capsule for the crystalline lens. However, such an intraocular lens has not yet been developed, and its production has been very difficult.

Under these circumstances, it is an object of the present invention to form an intraocular lens to be inserted and fixed in the lens capsule in the form of a hollow balloon having substantially the same shape as the crystalline lens so that it is capable of being snugly fit and held in the lens capsule and capable of being inserted even through a smaller incision than ever to solve the problem of the size of the incision.

Another object of the present invention is to provide processes for advantageously producing such a balloon for an intraocular lens.

The present invention provides a balloon for an intraocular lens, which is a unitary elastic hollow body made of an elastomer and having a convex lenticular shape without projections along its circumference, which gives, when inserted in a lens capsule, a configuration corresponding substantially to the shape of the lens capsule, said hollow body having a wall thickness of from 0.001 to 0.1 mm at its optical portion and a diameter of from 6 to 13 mm, and capable of being inflated in the lens capsule to form an intraocular lens when a light transmitting injection material is injected into the hollow body.

The present invention also provides a process for producing such a balloon for an intraocular lens, which comprises:

a step of preparing mold halves having mold cavities corresponding respectively to halves of a hollow made of an elastomer and having a convex lenticular shape, and having such balloon halves accommodated in the respective mold cavities;

a step of placing a predetermined amount of an adhesive monomer in one or each of the balloon halves, and closing the mold halves having the balloon halves accommodated therein so that the convex side of each balloon half is located outside and the peripheral edges of the balloon halves abut against each other; and a step of polymerizing the adhesive monomer while rotating the closed mold about an axis through the centers of the balloon halves, so that the abutting peripheral edges of the balloon halves are bonded by the polymer of the adhesive monomer.

The present invention provides another process for the production of such a balloon, which comprises:

a step of preparing a first mold half having a mold cavity corresponding to a half of a hollow made of an elastomer and having a convex lenticular shape, and having such a balloon half accommodated in the mold cavity;

a step of preparing a second mold half having a mold cavity corresponding to the other half of the hollow balloon, and closing the first and second mold halves with a predetermined amount of a balloon-forming monomer polymerizable to form an elastomer placed therein; and a step of polymerizing the monomer while rotating the closed mold about an axis through the center of the balloon half, so that the other half of the hollow balloon is formed in the second mold half and at the same time, the other balloon half is integrally bonded to the balloon half accommodated in the first mold half along the peripheral edge of the latter balloon half.

The present invention provides a further process for the production of such a balloon, which comprises:

a step of introducing a predetermined amount of a balloon-forming monomer polymerizable to form an elastomer into each of mold halves for halves of a hollow balloon having a convex lenticular shape, and casting the monomer on the surface of each mold;

a step of closing the mold halves with the cast monomer accommodated therein; and a step of polymerizing the monomer while rotating the closed mold, so that balloon halves are formed in the respective mold halves, and at the same time, the peripheral edges of the balloon halves are bonded to each other.

The present invention provides a still another process for the production of such a balloon, which comprises:

a step of introducing a predetermined amount of a balloon-forming monomer polymerizable to form an elastomer into a first mold half for a half of a hollow balloon having a convex lenticular shape, and casting the monomer on the surface of the first mold half;

a step of introducing a predetermined amount of a balloon-forming monomer polymerizable to form an elastomer into a second mold half for the other half of the hollow balloon, and overlaying the first mold half on the second mold half to close the mold halves; and a step of polymerizing the monomers while rotating the closed mold, so that balloon halves are formed in the respective mold halves, and at the same time, the peripheral edges of the balloon halves are bonded to each other.

Now, the present invention will be described in detail with reference to the preferred embodiments.

FIGS. 3(a)-(c) to 6(a)-(c) illustrate, respectively, different processes for advantageously producing the balloon for an intraocular lens of the present invention.

Figure 7:
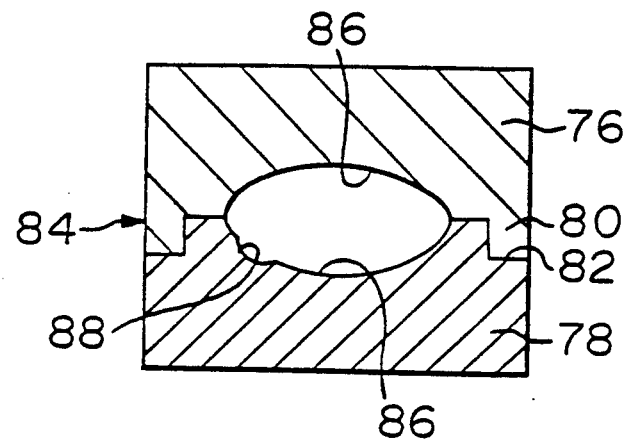
Figure 8:
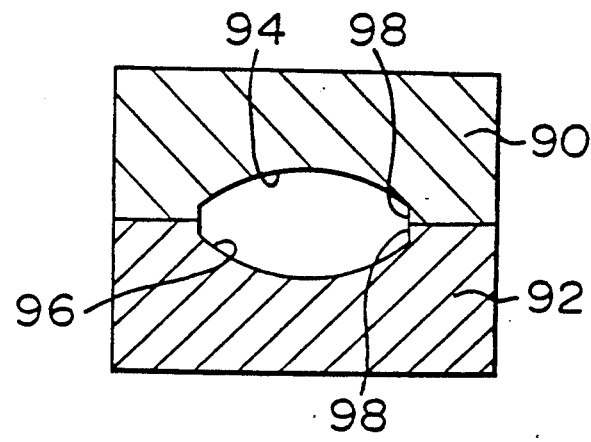
Figure 9:
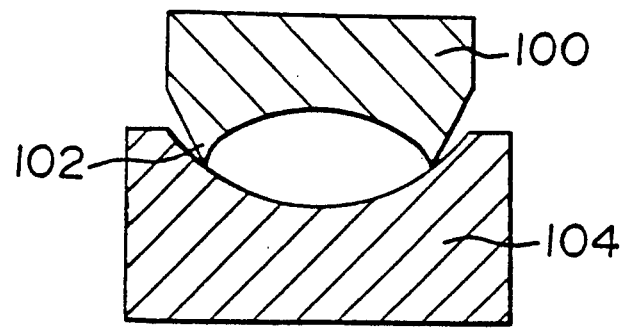

FIGS. 7 to 9 are cross-sectional views illustrating, respectively, different molds used for the preparation of the balloon for the intraocular lens of the present invention.

Figure 10:
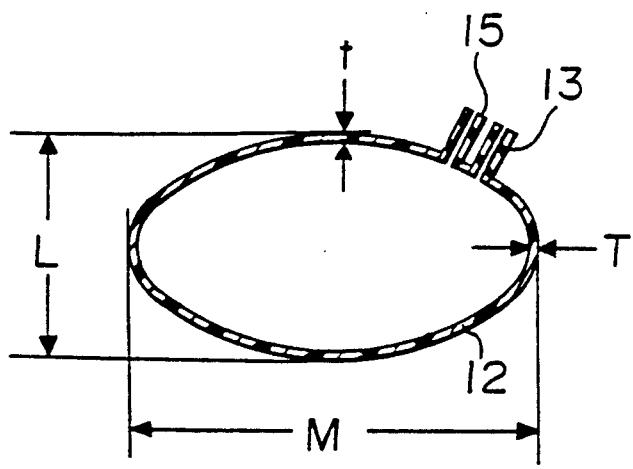

FIG. 10 is a cross-sectional view of a balloon for an intraocular lens of the present invention, which is provided with tubes for an inlet for an injection material and an outlet for discharging gas from the balloon.

Figure 11:
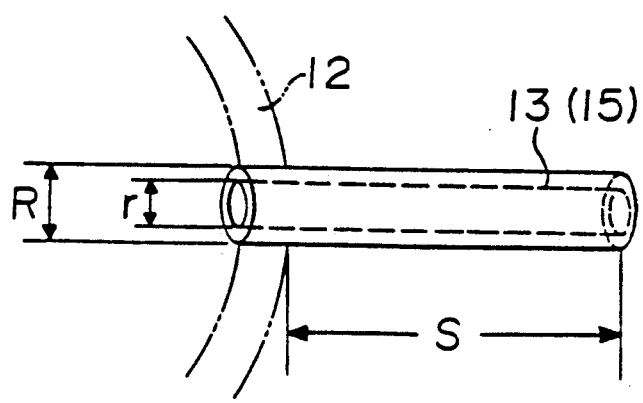

FIG. 11 is a perspective view of a tube as an embodiment of the inlet and the outlet of the balloon of the present invention.

Figure 12:
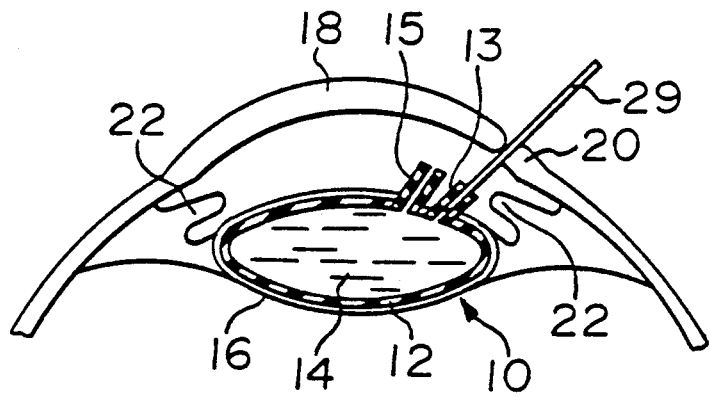

FIG. 12 is a cross-sectional view illustrating the state where an injection material has been injected into the balloon of FIG. 10.

Figure 13:
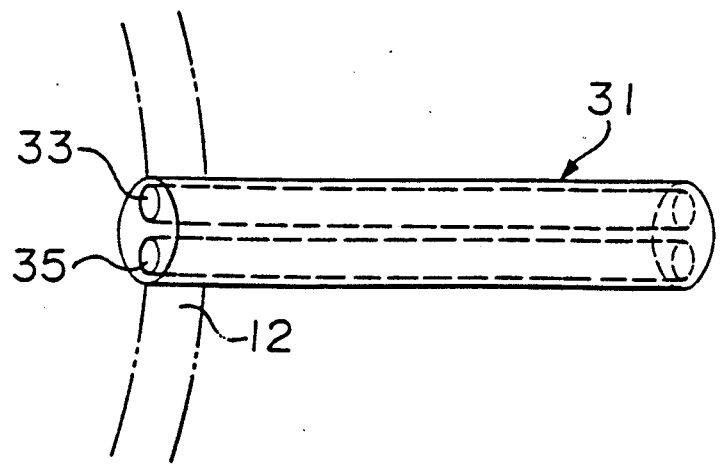

FIG. 13 is a perspective view of a tube as another embodiment of the inlet and outlet of the balloon of the present invention.

Figure 14:
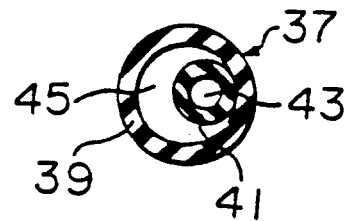

FIG. 14 is a cross-sectional view of a tube as a still another embodiment of the inlet and the outlet.

Figure 15:
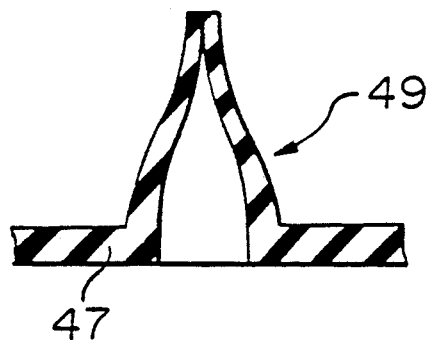

FIG. 15 is an enlarged cross-sectional view of a part of the balloon to illustrate a check valve as an embodiment of the outlet of the balloon of the present invention.

Figure 16A:
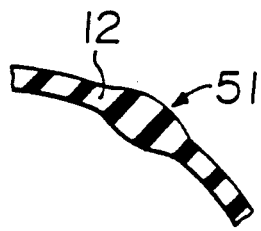

FIGS. 16(a) and (b) are enlarged cross-sectional views of parts of the balloons to illustrate thickened portions for inserting or attaching tubes of the balloons of the present invention.

FIGS. 17(a)-(d) are cross sectional views illustrating, respectively, the states where the inlet and the outlet are formed when a catheter is inserted into a tube of the balloon of the present invention.

Now, the present invention will be described in detail with reference to the drawings.

Figure 1:
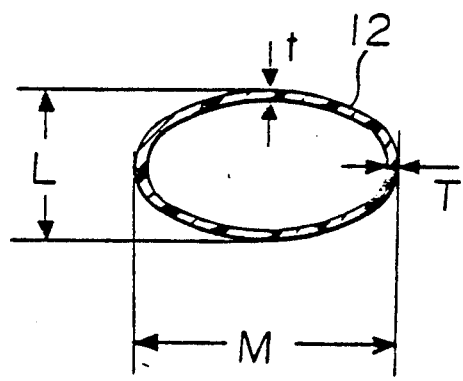
FIG. 1 is a cross-sectional view illustrating one embodiment of the balloon for an intraocular lens of the present invention.
Figure 2:
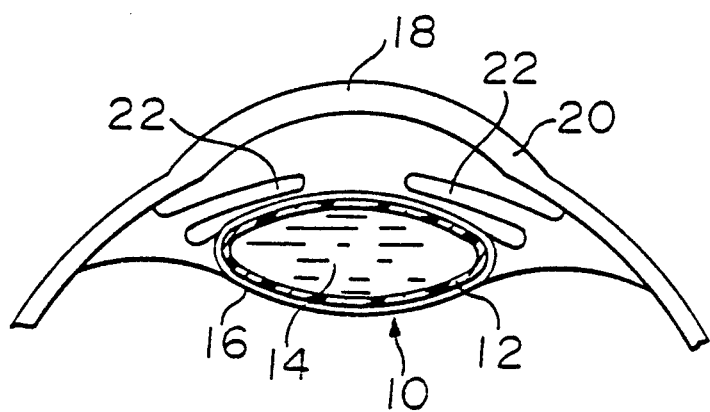
FIG. 2 is a cross-sectional view illustrating the state where the intraocular lens using the balloon of the present invention is implanted in the lens capsule for the crystalline lens.

Firstly, FIG. 1 illustrates an embodiment of the hollow balloon of the present invention, which gives a desired intraocular lens. Namely, the balloon 12 capable of providing such an intraocular lens, is made of a thin elastomer having elasticity and has a hollow convex lenticular shape. This balloon 12 is designed so that it is inserted into a lens capsule for a crystalline lens in a deflated state with gas discharged from the interior, and then an injection material 14 is injected to the interior by a usual injection operation by means of e.g. a catheter to form an intraocular lens 10 as shown in FIG. 2. Thus, it is held in place in the lens capsule 16, whereby the intraocular lens 10 effectively functions as a crystalline lens.

The balloon 12 constituting such an intraocular lens 10, is made of an elastomer and is expected to expand in the lens capsule upon the injection of a prescribed injection material Therefore, it is preferably expandable or stretchable by at least 50%. If the stretchability is less than 50%, it will be difficult to adequately expand the balloon in the capsule even when the injection material 14 is injected therein, and forcible expansion tends to lead to a deterioration of the balloon material, and such a balloon is likely to rupture at the time of its insertion into the capsule.

Further, such a balloon 12 is expected to provide a function as a crystalline lens together with the injection material 14 injected therein. Therefore, it is naturally required to be made of a material having good light transmittance In general, it is made of a material having a transparency at a level of a visual light transmittance (a transmittance in a range of from 380 to 780 nm) of at least about 65%. Further, it is preferably made of a non-water absorptive material to prevent elution of the injection material 14 into the eye or to prevent accumulation in the material of a residue of an aqueous humor.

In order to satisfy such requirements, the balloon 12 is preferably made of a material such as polyurethane, silicone rubber, segmented polyurethane or a block or graft copolymer of polysiloxane with polyurethane.

If necessary, additives which are commonly employed, such as a dye and a ultraviolet absorber may be incorporated to the above material for the balloon 12.

The balloon for an intraocular lens of the present invention is a unitary hollow body having a convex lenticular shape without projections along its circumference, which some conventional intraocular lenses used to have as means for fixing the lenses in the lens capsules. Namely, the balloon of the present invention has substantially the same shape as a crystalline lens, as shown in FIG. 1. Thus, the intraocular lens 10 can be effectively held in close contact with the inner suface of the lens capsule for a crystalline lens 16. At the same time, it is possible to effectively prevent the leakage of the injection material 14 injected into the balloon 12 from the injection hole out of the intraocular lens 10.

With respect to the size of the balloon 12, its optical portion i.e. the light transmitting central portion has a wall thickness of from 0.001 to 0.1 mm. Therefore, if the internal gas (air) is removed, the balloon can be folded into a small size and thus can be inserted into the lens capsule even from a small incision. If the wall thickness is less than 0.001 mm, the wall tends to be susceptible to rupture. On the other hand, if the wall thickness is more than 0.1 mm, the insertion into the capsule tends to be difficult, and it also becomes difficult to let the balloon in the capsule conform to the shape of the capsule. From the efficiency for the insertion, the wall thickness is preferably from 0.005 to 0.05 mm. The wall thickness of the optical portion except for the peripheral portion of the balloon 12 is preferably substantially uniform However, the central portion may preferably be slightly thinner.

The diameter (M in FIG. 1) of the balloon 12 is from 6 to 13 mm, so that the diameter would be substantially the same as the diameter of the lens capsule when the injection material has been injected into the capsule. The thickness (L in the FIG. 1) of the balloon is preferably from 2 to 6 mm, so that it is substantially the same as the thickness of the lens capsule when the injection material has been injected into the capsule.

The wall thickness (T in FIG. 1) at the peripheral portion of the convex lenticular shape of the balloon 12 is preferably from 1.1 to 4.0 times the wall thickness of the optical portion (the central portion) of the balloon 12. Namely, the wall thickness of the peripheral portion is made slightly thicker so that the configuration of the intraocular lens 10 can be maintained to be similar to the shape of the crystalline lens even when the injection material 14 has been injected.

On the other hand, the injection material 14 to be injected in the balloon 12, is expected to let the balloon 12 expand in the lens capsule 16 to a size substantially equal to the crystalline lens and to let it form an intraocular lens 10 functioning as a crystalline lens. Therefore, the injection material is desired to be a light transmitting fluid, particularly a transparent liquid. Usually, it is preferred to employ a material having a refractive index of at least 1.36. With respect to the viscosity, it is usually advantageous to employ a material having a viscosity of not higher than about 300,000 centipoise to avoid a difficulty in the injection into the balloon 12. As the injection material 14 having such properties, it is possible to employ, for example, a solution or cross linked gel of a polysaccharide such as cellulose, chitin, arginic acid or hyaluronic acid, or its derivative, a solution of a synthetic polymer electrolyte such as polyacrylic acid, polyacrylamide propylsulfonic acid or polystyrene sulfonic acid, a solution of a water-soluble oligomer such as hydroxyethyl methacrylate, N vinyl pyrrolidone or polyvinyl alcohol, silicone oil or silicon gel. These components may be injected or gelled in the balloon 12 for accommodation in the balloon 12. Such a injection material 14 is injected in an amount sufficient to fill the capacity of the crystalline lens and is usually from about 0.1 to 0.3 ml.

To implant the balloon 12 of the present invention as an intraocular lens 10 in the lens capsule for a crystalline lens (see FIG. 2), firstly, a cataractous crystalline lens portion is removed to leave the lens capsule 16, with due care not to damage the iris 22, etc., through an incision provided as small as possible at a predetermined position of the sclera 20 located around the cornea 18. On the other hand, a catheter is inserted into the balloon 12, and air in the balloon 12 is discharged, whereupon the balloon is folded into a small size. Then, the balloon 12 having such a catheter attached, is inserted into the lens capsule 12 through an incision of the sclera and through an incision of the capsule. Then, a predetermined injection material 14 is injected through the catheter into the balloon 12, whereupon the balloon 12 is inflated to be in close contact with the entire inner surface of the lens capsule 16 to form an intraocular lens 10. Thus, the intraocular lens is snugly fit and fixed in the capsule.

After completion of the injection of such an injection material 14, the catheter is withdrawn from the balloon 12, and the incision of the sclera is sutured, whereby the intraocular lens 10 is implanted as shown in FIG. 2. Since the balloon 12 is closely in contact with the lens capsule, there will be no leakage of the injected material from the injection hole even when the catheter is withdrawn.

In addition to the fact that the balloon 12 (the intraocular lens 10) is closely fit and fixed over the entire inner surface of the lens capsule 16, its wall thickness is thin, whereby the intraocular lens 10 is capable of efficiently following the movement of the capsule, and the visual control similar to a natural eye is thereby possible Thus, the intraocular lens 10 effectively functions as an artificial crystalline lens.

Such a balloon for an intraocular lens of the present invention can be advantageously produced by any one of the following processes.

Firstly, FIGS. 3(a)–(c) illustrate a process for advantageously producing the balloon 12 of the present invention.

In these Figures, reference numeral 24a designates a mold half having a mold cavity 26a corresponding to a half of the balloon 12. Namely, this mold cavity 26a has a configuration to give the shape of one side of the balloon 12 (the outer surface of the half of the balloon), which corresponds to one side of the convex lenticular shape i.e. to the shape of one side of the crystalline lens. In such a mold half 24a, a balloon half 28a is formed by a usual molding method, an injection molding method or a spin casting method, or a separately formed balloon half 28a is placed in the cavity 26a of the mold half 24a. Thus, the mold half 24a having the balloon half 28a accommodated in the mold cavity is prepared (see FIG. 3(a)).

In the same manner, a mold half 24b having a balloon half 28b accommodated in a mold cavity 26b to give the shape of the other half of the balloon 12, is prepared At least the diameters of the mold cavities 26a and 26b of these mold halves 24a and 24b are the same.

The material for such balloon halves 28a and 28b is preferably the same as used for the above described balloon 12. Usually, its monomer is polymerized by heat or by ultraviolet rays to form the balloon halves 28a and 28b. As the material for mold halves 24a and 24b, it is common to employ a metal or a plastic, and a light transmitting plastic is preferably employed when polymerization is conducted by ultraviolet rays.

Then, a predetermined amount of an adhesive monomer 30 is placed in one or each of the mold cavities of the mold halves 24a and 24b. Such an adhesive monomer 30 is naturally selected from those having good adhesion to the balloon halves 28a and 28b. In order to maintain the properties of the balloon, it is preferred to employ a monomer which provides a polymer having a stretchability of at least about 50%. Thermosetting or ultraviolet curable silicone or urethane monomers may be mentioned as specific examples of such a monomer. However, the light transmittance is not critical, since such an ahesive monomer 30 will be present only along the peripheral portion of the balloon.

Then, the mold halves 24a and 24b having the balloon halves 28a and 28b accommodated therein, are, after the placement of such an adhesive monomer 30, closed coaxially so that the convex side of each of the balloon halves 28a and 28b is located outside and the peripheral edges of the balloon halves 28a and 28b abut against each other (see FIG. 3(b)).

Under such a condition, the closed mold halves 24a and 24b are rotated about an axis (axis O) at a predetermined rotational speed, whereby the adhesive monomer 30 is gathered to the bonding portion along the peripheral edges of the balloon halves 28a and 28b by the centrifugal action and polymerized under the action of heat or ultraviolet rays to form a bonding layer 32. Thus, the balloon halves 28a and 28b are bonded along their peripheral edges (see FIG. 3(c)). In this manner, the balloon 12 for an intraocular lens of the present invention is advantageously produced.

Figure 4A:
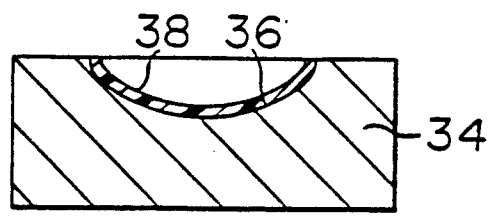
Figure 4B:
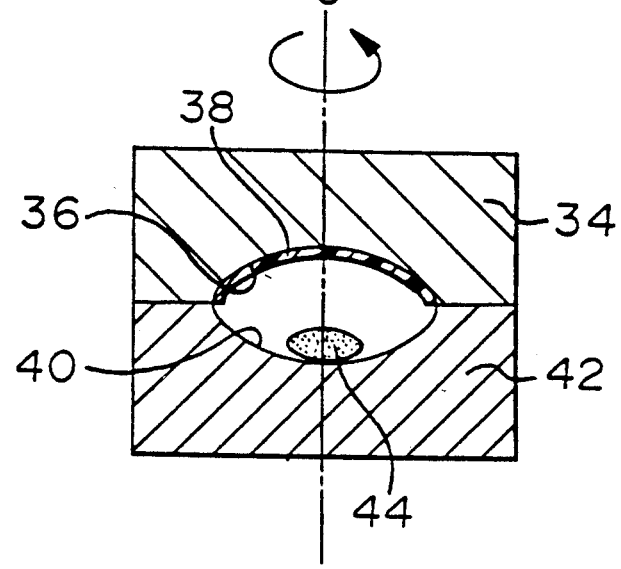
Figure 4C:
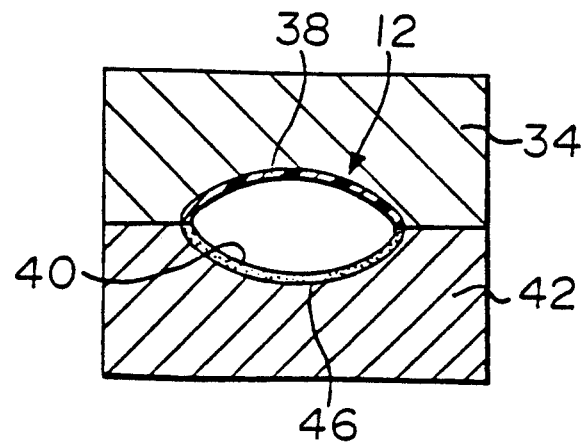

Now, another process for advantageously producing the balloon of the present invention will be described with reference to FIGS. 4(a)-(c).

Firstly, reference numeral 34 is a first mold half having a mold cavity 36 corresponding to the shape of one side of the balloon, like the above-mentioned mold halves 24a and 24b. Such a cavity 36 has a concave surface corresponding to one side of the convex lenticular shape i.e. to the shape of one side of the crystalline lens, like the above mentioned mold cavities 26a and 26b.

In the same manner as described above, in such a mold half 34, a balloon half 38 is formed by a usual molding method, an injection molding method or a spin casting method, or a separately formed balloon half 38 is placed in the mold cavity. Thus, a first mold half 34 having a balloon half 38 accommodated therein, is prepared (see FIG. 4(a)).

On the other hand, a second mold half 42 having a cavity 40 designed to give the shape of the other side of the balloon 12, is prepared. At least the diameters of the mold cavities 36 and 34 of such first and second mold halves 34 and 42, are the same.

The material for such a balloon half 38 is preferably the same as the above-mentioned material used for the balloon 12. Usually, its monomer is polymerized by heat or ultraviolet rays to form the balloon half 38. The material for such mold halves 34 and 42 is usually a metal or a plastic, and a light transmitting plastic is preferably employed in the case where polymerization is conducted by ultraviolet rays.

Then, a predetermined amount of a balloon-forming monomer 44 is placed in the cavity 40 of the second mold half 42. Such a balloon-forming monomer 44 is preferably a monomer for the above-mentioned material for the balloon. The balloon-forming monomer 44 is required to provide adhesion to the balloon half 38. Particularly preferred are thermosetting or ultraviolet curable silicone or urethane monomers After placing such a balloon-forming monomer 44 in the cavity 40 of the second mold half 42, the first mold half 34 having the balloon half 38 accommodated therein is overlaid on the second mold half 42 coaxially so that the convex surface of each of the cavities 36 and 40 is located outside, and the peripheries of the cavities 36 and 40 agree to each other (see FIG. 4(b)).

Under such a condition, the closed mold halves 34 and 42 are rotated about an axis (axis O) at a predetermined rotational speed, and while controlling the rotational speed, the balloon-forming monomer 44 is spread substantially uniformly in the mold cavity 40 of the second mold half 42 by the centrifugal action. At that time, the monomer is polymerized under the action of heat or ultraviolet rays to form a balloon half 46 having the shape of the other side of the balloon. At the same time, the monomer is polymerized and bonded along the periphery of the balloon half 38 accommodated in the first mold half 34 located above, whereby the balloon halves 38 and 46 are bonded integrally (see FIG. 4(c)). Thus, the balloon 12 for an intraocular lens of the present invention is advantageously produced.

Figure 5A:
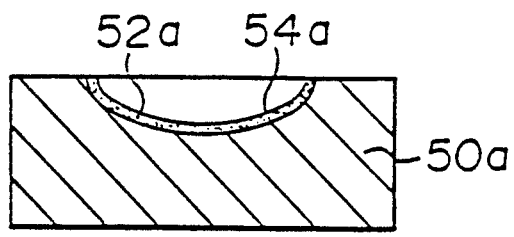

Further, another process for advantageously producing the balloon of the present invention will be described with reference to FIGS. 5(a)-(c).

Firstly, reference numeral 50a designates a mold half having a mold cavity 52a corresponding to the shape of one side of the balloon, like the above-mentioned mold halves 24a and 24b. In such a mold half 50a, a balloon-forming monomer 54a is cast on the surface of the cavity 52a to form the shape of a balloon half (see FIG. 5(a)). Such casting may be conducted in such a manner that the balloon-forming monomer is placed in the cavity 52a, and the mold half 50a is rotated to cast the monomer by the centrifugal action.

In the same manner, a balloon-forming monomer 54b is cast in a mold half 50b having a mold cavity 52b corresponding to the shape of the other side of the balloon 12. At least the diameters of the cavities 52a and 52b of the two mold halves 50a and 50b, are the same.

Figure 5B:
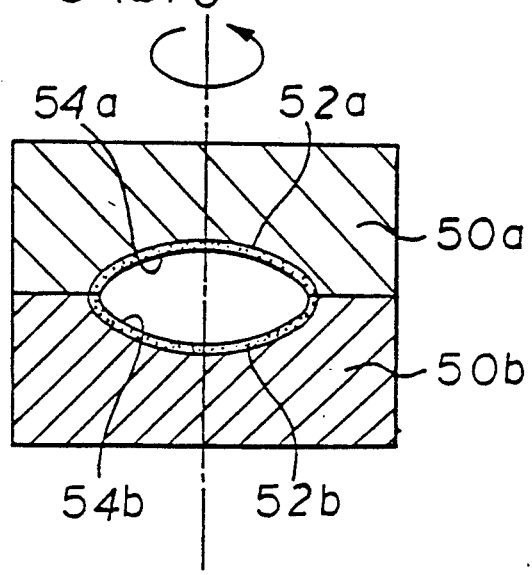
Figure 5C:
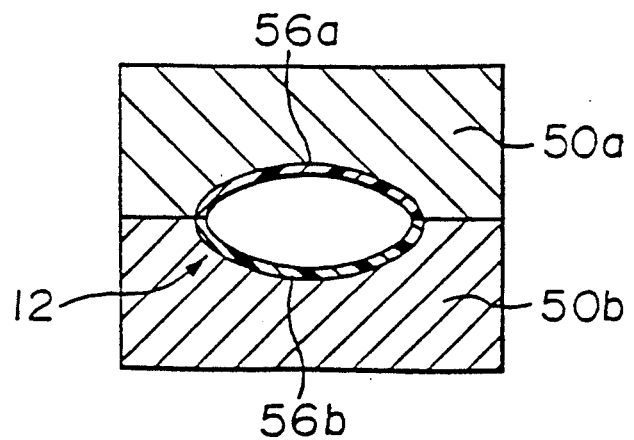

Then, these mold halves 50a and 50b are closed coaxially so that the convex surface of each of the cavities 52a and 52b is located outside and the peripheries of these cavities agree to each other (see FIG. 5(b)).

Such balloon-forming monomers 54a and 54b are preferably the same monomer as described above as the material for the balloon. The monomers are required to have a certain viscosity since the mold halves 50a and 50b are overlaid one on the other or one at the left and the other at the right. Specifically, the monomers preferably have a viscosity of at least about 100 cps. If the viscosity is less than 100 cps, it is likely that an optical surface can not be formed by the rotation of the closed mold halves. Therefore, there is no such a problem if a highly viscous monomer is employed. A monomer having a low viscosity may be polymerized to some extent to increase the viscosity (to form a prepolymer) before use. The material for such mold halves 50a and 50b is usually a metal or a plastic, and a light transmitting plastic is preferably employed in a case where polymerization is conducted by ultraviolet rays.

Under such a condition, the closed mold halves 50a and 50b are rotated about an axis (axis O) at a predetermined rotational speed. While controlling the rotational speed to maintain the shape of the balloon halves, the balloon-forming monomers 54a and 54b are polymerized, and at the same time, the balloon-forming monomers 54a and 54b cast in the respective cavities 52a and 52b are polymerized and bonded along the peripheral edges, whereby the balloon halves 56a and 56b are formed and integrally bonded (see FIG. 5(c). Thus, the balloon 12 for an intraocular lens of the present invention is effectively produced.

A still another process for advantageously producing the balloon of the present invention will be described with reference to FIGS. 6(a)-(c).

Firstly, reference numeral 60 is a first mold half having a mold cavity 62 corresponding to one side of the balloon, like the above mentioned mold halves 24a and 24b In such a mold half 60, a balloon-forming monomer 64 is cast on the surface of the cavity 62 in the form of the balloon half (see FIG. 6(a)). Such casting is preferably conducted in such a manner that the balloon-forming monomer 64 is placed in the cavity 62, and the mold half 60 is rotated to cast the monomer by the centrifugal action.

Then, a second mold half 68 having a mold cavity 66 corresponding to the shape of the other side of the balloon, is prepared. At least the diameters of the cavities 62 and 66 of such first and second mold halves 60 and 68, are the same.

Then, a predetermined amount of a balloon-forming monomer 70 is placed in the mold cavity 66 of the second mold half 68. Then, the first mold half 60 having the balloon-forming monomer 64 cast therein, is overlaid on the second mold half 42 coaxially, so that the convex surfaces of each of the cavities 62 and 66 is located outside, and the peripheries of the cavities agree to each other (see FIG. 6(b)).

Such balloon-forming monomers 64 and 70 are preferably the same as mentioned above as the monomer for the balloon. Such a balloon-forming monomer 64 is required to have a viscosity to some extent since, as in the case of FIG. 5, the mold half 60 is overlaid on the mold half 68. Specifically, the monomer is preferably the one having a viscosity of at least about 100 cps. If the viscosity is less than 100 cps, an optical surface may not be formed even when the closed mold halves are rotated. If a monomer having a high viscosity is employed, there will be no such a problem. A monomer having a low viscosity may be polymerized to some extent to increase the viscosity before use. The material for the mold halves 60 and 68 is usually a metal or a plastic, and a light transmitting plastic is preferably employed in a case where polymerization is conducted by ultraviolet rays.

Under such a condition, the closed mold halves 60 and 68 are rotated about an axis (axis 0) at a predetermined rotational speed, and while controlling the rotational speed so that the balloon-forming monomer 64 in the first mold half 60 is maintained in the form of the balloon half, the balloon-forming monomer 70 is spread substantially uniformly in the cavity 66 of the second mold half 68 by the centrifugal action. The balloon-forming monomers 64 and 70 are polymerized under the action of heat or ultraviolet rays, and at the same time, the balloon-forming monomer 70 is bonded along the peripheral edge of the balloon-forming monomer 64 cast in the first mold half 60 located above, whereby balloon halves 72 and 74 will be formed and bonded integrally (see FIG. 4(c)). Thus, the balloon 12 for an intraocular lens of the present invention is effectively produced.

In the foregoing, several processes for advantageously producing the balloon for an intraocular lens of the present invention, have been described. By employing such processes, the balloon for an intraocular lens of the present invention can be produced simply and at a low cost.

For the polymerization of the adhesive monomer or the balloon-forming monomer, heat polymerization or ultraviolet polymerization is usually preferably employed. More specifically, the heat polymerization is conducted usually at a temperature of from room temperature to 150° C. from 5 minutes to 24 hours, and the ultraviolet polymerization is conducted usually for a period of from 10 seconds to 10 minutes by using a usual light source such as a high pressure mercury lamp. The rotational speed of the mold halves is usually from 100 to 10,000 rpm. However, it is properly selected depending upon the process for the production of the balloon and on the viscosity of the monomer used.

With respect to the configuration of the mold halves, various configurations may be employed in addition to those shown in FIGS. 3 to 6. For example, as shown in FIG. 7, it is possible to employ a male-female meshing mechanism 84 comprising the circumferential projection 80 of the mold half 76 and the circumferential recess 82 of a mold half 78, so that the mold halves 76 and 78 can easily be meshed. However, without such a male-female meshing mechanism 84, the balloon half-forming surfaces may be brought in agreement by e.g. a jig or the like.

Further, in order to provide a thickened portion without bringing about an adverse effect to the optical portion of the balloon, a recess 88 having a predetermined depth and size may be formed in the mold cavity 86 of the mold half 78. By forming a balloon by means of such mold halves 76 and 78, it is possible to make the wall thickness of the balloon partially thick, and the thickened portion may be used for insertion of a catheter for injecting a injection material, so that when the catheter is withdrawn, the balloon will have a self sealing property.

Further, in a case of forming a balloon having a diameter smaller than the diameter of the lens capsule, in order to conform the balloon better to the shape of the capsule, the peripheral portions of the cavities 94 and 96 of the mold halves 90 and 92 may be made cylindrical vertical surfaces 98 and 98, so that the bonding portions of the balloon halves may be somewhat cylindrical, as shown in FIG. 8.

Further, in order to minimize formation of a flash along the bonding portion of the balloon halves, the circumferential edge of the balloon half-forming surface of a mold half 100 is made an annular projection 102, so that the contact between the mold halves 100 and 104 will be a line contact, as shown in FIG. 9.

Furthermore, by using a mold whereby a catheter for injecting a injection material can be set, it is possible to set such a catheter to the mold during the formation of the balloon, so that the catheter is inserted and fixed to the balloon at the same time as the formation of the balloon.

Now, some Examples will be given for the production of a balloon for an intraocular lens in accordance with the processes of the present invention.

EXAMPLE 1

In accordance with the process as shown in FIG. 3, a balloon for an intraocular lens was prepared Firstly, 5 mg of a RTV (room temperature vulcanizable) silicone monomer was dropped in the cavity of a first mold half of PMMA corresponding to the shape of one side of the balloon. This mold half was heated while being rotated at a speed of 1,300 rpm, whereby a balloon half was polymerized and formed under heating to 70° C. In the same manner, a balloon half was formed in another mold half, and 2 mg of a silicone monomer was dropped in the mold cavity of the second mold half having the balloon half formed therein Then, to this second mold half, the first mold half having the balloon half attached thereto, was overlaid. The closed mold was heated at 70° C. for 30 minutes while being rotated at 1,600 rpm. Then, the formed balloon was detached from the mold halves, to obtain a balloon for an intraocular lens having a diameter of about 10 mm and a wall thickness of from 0.01 to 0.02 mm, with the two balloon halves completely bonded to each other.

EXAMPLE 2

In accordance with the process as shown in FIG. 4, a balloon for an intraocular lens was prepared Firstly, 5 mg of a prepolymer of a two liquid type room temperature vulcanizable polyurethane, was dropped into a cavity of a mold half of brass corresponding to the shape of one side of the balloon. The mold half was heated to 140° C. while being rotated at a speed of 1,200 rpm, and a balloon half was polymerized and formed under heating. Then, 8 mg of a prepolymer of a two liquid type room temperature vulcanizable polyurethane was dropped in the cavity of another mold half for the other half of the balloon. To this mold half, the above mold half having the balloon half attached thereto, was overlaid. The closed mold was heated from room temperature to 140° C. for a period of 60 minutes while being rotated at a speed of 1,700 rpm, for polymerization under heating. Then, the formed balloon was detached from the mold halves, to obtain a balloon for an intraocular lens having a diameter of about 10 mm and a wall thickness of from 0.01 to 0.02 mm with the two balloon halves completely bonded to each other.

EXAMPLE 3

Figure 6:
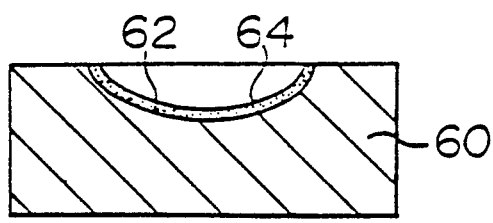
Figure 6:
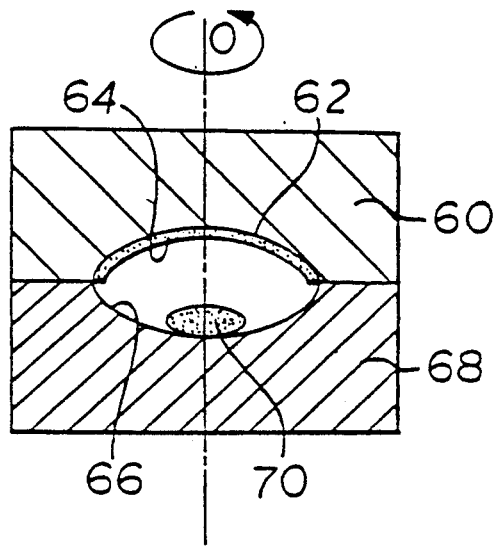
Figure 6:
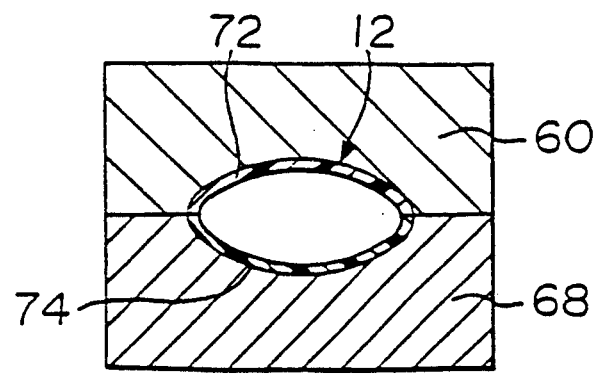

In accordance with the process as shown in FIG. 6, a balloon for an intraocular lens was prepared Firstly, 5 mg of a ultraviolet curable silicone monomer was dropped in a cavity of a mold half of PMMA corresponding to the shape of one side of the balloon. This mold half was rotated at a speed of 1,600 rpm to form a balloon half in a non-polymerized state. Then, 7 mg of a ultraviolet curable silicone monomer was dropped into the cavity of another mold half for the other half of the balloon. To this mold half, the above mold half was swiftly overlaid, and ultraviolet rays were irradiated for 5 minutes while rotating the closed mold at a speed of 1,600 rpm. Then, the formed balloon was detached from the mold halves to obtain a balloon for an intraocular lens having a diameter of about 10 mm and a wall thickness of from 0.01 to 0.02 mm with the two balloon halves completely bonded to each other.

The balloon of the present invention can be folded into a small size after discharging gas such as air from the interior and can be inserted into the lens capsule in the folded state. Therefore, the incision of the sclera for the insertion can be made small. On the other hand, the balloon has a configuration corresponding substantially to a crystalline lens, and upon the injection of an injection material, it is effectively fixed in the capsule to form an intraocular lens capable of following the movement of the capsule, whereby the vision can be controlled like a natural eye.

However, it is practically rather difficult and cumbersome to completely remove the gas (air) from the interior of the balloon prior to the insertion of the balloon into the lens capsule. If air bubbles remain in the intraocular lens formed by the injection of the injection material into the balloon, it is likely that an optical inconvenience will result due to the air bubbles remaining in the interior of the intraocular lens. In order to solve such a problem, according to a preferred embodiment of the present invention, the balloon is provided with an inlet for the injection material and an outlet for discharging gas from the balloon.

Such inlet and outlet are preferably constituted by separate tubes.

Otherwise, such inlet and outlet may be constituted by two pathways formed in one tube.

Further, the outlet may be constituted by a check valve or a gas permeable membrane integrally provided on the wall of the balloon.

In another embodiment of the invention, the balloon has a tube having an inner diameter larger than the outer diameter of a catheter and provided therein with a supporting portion for holding the catheter. A catheter is inserted in the tube and held by the supporting portion so that said inlet is constituted by the catheter and said outlet is constituted by the space between the outer surface of the catheter and the inner wall of the tube.

Specific embodiments for the inlet and the outlet will be described with reference to the drawings.

Firstly, referring to FIG. 10, a hollow balloon body 12 is provided with tubes 13 and 15. One of the two tubes is an injection tube (13), and the other is a discharge tube (15). The balloon 12 is made of an elastomer having elasticity and is a hollow body having a convex lenticular shape corresponding substantially to a crystalline lens without projections along the circumference.

The balloon 12 is deflated with air discharged from the interior and in that deflated state, inserted in the lens capsule for a crystalline lens. Then, an injection material 14 is injected into the balloon 12 through the tube 13, and at the same time, a gas such as air remaining in the balloon is discharged through the tube 15 (see FIG. 12). Then, the tubes 13 and 15 are cut and sealed to form an intraocular lens 10 as shown in FIG. 2. Thus, the intraocular lens 10 is held in the lens capsule 16 and effectively functions as an artificial crystalline lens.

Thus, in the above mentioned embodiment, the inlet and the outlet are constituted by separate tubes 13 and 15. Such tubes 13 and 15 may be made of a material which is not transparent However, in order to minimize an influence to the optical portion (pupil region), it is preferred to employ a transparent material. Further, the material is preferably flexible from the viewpoint of the effect to the lens capsule 16 or the operation efficiency for the injection of the injection material 14 into the balloon 12. Specifically, in addition to the abovementioned material for the balloon, elastomers such as silicone, urethane, polyvinyl chloride, polyester and fluorine rubber, or a thin polyolefin such as polypropylene and a fluorocarbon such as polytetrafluoroethylene, may be mentioned. These tubes 13 and 15 may be integrally formed when the balloon 12 is molded. Otherwise, they may be attached to the balloon 12 already molded.

With respect to the size of such injection tube 13, as shown in FIG. 11, the outer diameter R is usually at most 3 mm, preferably at most 2 mm from the viewpoint of the operation efficiency for the insertion of the balloon 12 into the lens capsule 16 or for the injection of the injection material 14 into the balloon 12. On the other hand, the inner diameter r is usually at least 0.05 mm, preferably at least 0.1 mm so that the injection material 14 can be injected without difficulty. The length S projecting from the balloon 12 is usually at least 1 mm, preferably at least 2 mm to facilitate the injection operation from outside the lens capsule 16. The size of the discharge tube 15 may substantially be the same as the injection tube 13. If the end of the discharge tube 15 is projected too much in the interior of the balloon 12, the air in the interior tends to be hardly discharged. Therefore, the tube 15 is preferably not to project too much inwardly. Preferably, as shown in FIG. 11, it is attached so that the end is flush with the inner surface of the balloon 12.

As to the attaching positions of the tubes 13 and 15 to the balloon 12, it is preferred to attach them at the front side of the balloon 12 from the viewpoint of the operation efficiency for the injection of the injection material and for the reason that at the time of the implantation operation, air tends to remain at an upper portion (the front side). Further, taking the effect to the vision into consideration, it is advisable to provide them outside the optical portion. Namely, they may preferably be located at least 1.5 mm, more preferably at least 2 mm away in the radial direction from the center of the balloon 12. To implant such a balloon 12 as an intraocular lens 10 in the lens capsule 16 (see FIGS. 2 and 12), firstly, the cataractous crystalline lens portion is removed leaving the lens capsule 16, with due care not to damage the iris 22, etc., through an incision formed as small as possible at a predetermined portion of the sclea 20 located around the cornea 18. On the other hand, a catheter 29 is inserted to the tube 13 attached to the balloon 12. Air is discharged from the balloon 12, and the balloon 12 is folded into a small size. The balloon 12 provided with such a catheter 29 is inserted into the lens capsule 16 through an incision of the sclea and through the incision of the lens capsule. The tube 15 for discharging air is disposed to protrude from the capsule. Then, as shown in FIG. 12, a predetermined injection material 14 is injected into the balloon 12 through the catheter 29, whereby the balloon 12 is expanded to fit over the entire inner surface of the lens capsule 16. On the other hand, air remained in the balloon 12 is discharged from the tube 15, and the interior of the balloon is filled with the injection material 14 to form an intraocular lens 10. Thus, the intraocular lens 10 is fixed in the lens capsule.

After completion of the injection operation and the operation to discharge air, the catheter 29 is withdrawn from the balloon 12 (the tube 13), and the extra portions (projections) of tubes 13 and 15 are cut off by scissors, heat or a laser, and the cut portions are sealed if necessary. Then, the incision of the sclera is sutured to complete the implantation of the intraocular lens 10 as shown in FIG. 2. Further, if a polymerizable material such as a polymerizable silicone is employed as the injection material 14, and it is capable of being readily polymerized, no sealing may be necessary, since there will be no leakage of the injected material 14.

With the construction as described above, it is possible to discharge air remaining in the balloon from the outlet (tube 15) while injecting the injection material 14 through the inlet (tube 13), whereby no optical problem due to air bubbles remaining in the intraocular lens will result. Further, it is unnecessary to completely discharge air from the balloon 12 prior to the insertion of the balloon into the lens capsule 16, whereby the discharging operation can easily be conducted.

Further, as the inlet, the tube 13 is employed, whereby formation of air bubbles during the injection of the injection material 14 can be minimized. Further, the catheter 29 can be securely held to the balloon 12 through the tube 13, whereby slipping off of the catheter 29 can be prevented, and the insertion of the balloon 12 into the lens capsule is facilitated. Further, with the length of the tube 13, it becomes possible to inject the injection material from outside the capsule 16 or from outside the eye. Furthermore, by utilizing the surgery hole (with a small diameter) formed for the removal of the crystalline lens, the balloon 12 may be inserted by means of the tube 13 without using the catheter. Further, as the outlet, the tube 15 is employed, whereby air remaining in the balloon 12 can be effectively led to outside the lens capsule for discharge.

Now, other embodiments of the inlet and the outlet of the balloon of the present invention will be described.

Firstly, FIG. 13 shows a tube 31 provided on the balloon 12. In the tube 31, independent two pathways are formed. One of the pathways serves as injection hole 33 as the inlet, and the other serves as a discharge hole 35 as the outlet.

FIG. 14 is a cross-sectional view of a tube 37 has another embodiment. Such a tube 37 comprises an outer tube 39 and an inner tube 41 having an outer diameter which is smaller than the inner diameter of the outer tube 39. The tubes 39 and 41 are in contact and fixed to each other at the inner surface of the outer tube 39 and at the outer surface of the inner tube 41, whereby a pathway 43 is formed in the inner tube 41, and a pathway 45 is formed between the inner tube 41 and the outer tube 39. As in the case of the above tube 31, the inlet and outlet are constituted by the pathways 43 and 45, respectively, in one tube 37. These tubes 31 and 37 may be integrally formed at the time of forming the balloon, or they may be attached to the balloon 12 already molded, as in the case of the above-mentioned tubes 13 and 15.

The material for such tubes 31 and 37 may be the same as the material for the above-mentioned tubes 13 and 15 for the same reason as mentioned above. With respect to the size of these tubes 31 and 37, the outer diameter is usually at most 3 mm, preferably at most 2 mm for the same reason as described above. On the other hand, the inner diameter of the pathway is usually at least 0.05 mm, preferably at least 0.1 mm (provided that in the case where the pathway 46 is an inlet, the cross-sectional area is adjusted to be equal). The length protruding from the balloon 12 is usually at least 1 mm, preferably at least 2 mm. If the end of the tube 31 or 37 protrudes too much in the balloon 12, air in the interior is hardly discharged. Therefore, like the tube 15, the tube 31 or 37 is attached not to protrude too much inwardly. Preferably, as shown in FIG. 13, it is attached to the valve 12 so that the end portion is flush with the inner surface of the balloon.

After completion of the injection operation and the operation to discharge air, extra portions of the tubes are cut off by scissors, heat or a laser, and the cut portions are sealed, if necessary.

As another embodiment of the outlet, FIG. 15 shows a check valve 49 formed integrally with the wall 47 of the balloon. Such a check valve 49 is provided to protrude outwardly from the balloon, so that air in the interior of the balloon can be discharged to the exterior, but entry of air from the exterior to the interior is prevented. As the check valve 49, any conventional check valve such as an umbrella type or a duck bill type may be employed. Among them, the duck bill type is preferably employed in that the outer diameter can thereby be made small. The size of the check valve 49 is desired to be as small as possible. Usually, its diameter is preferably at most about 2 mm, and the length is at most about 3 mm. Such a check valve 49 may be the one attached to a balloon which has been independently formed.

Further, as the outlet, it is possible to employ a gas permeable membrane which permits air to pass but which does not permit the injection material to pass. As such a gas permeable membrane, a hydrophobic porous membrane such as a fluorine resin membrane, a porous membrane of e.g. polyolefin or a fluorocarbon or a bundle of hollow fibers formed into a thin membrane, may be employed. Such a gas permeable membrane may be integrally formed at the time of forming the balloon, or may be attached to a balloon independently formed. The size is at most 4 mm in diameter. Such a tube 31, 37 or a check valve 49 or a gas permeable membrane, is preferably provided on the front side of the balloon 12 at a location displaced radially outwardly by at least 1.5 mm, preferably at least 2 mm from the center, like the above-mentioned tubes 13 and 15. They are naturally disposed or exposed outside the lens capsule during the injection operation.

It is thereby possible to discharge remaining air as far as possible, whereby no optical problem due to remaining air bubbles will remain. Further, it is unnecessary to completely remove air from the interior prior to the insertion of the balloon into the lens capsule 16. Therefore, the deaeration operation can be simplified. By using a tube 31 or 37 for such inlet and outlet, formation of air bubbles during the injection of the injection material 14 can be reduced. Further, a catheter can thereby be effectively held, whereby the insertion of the balloon into the capsule is facilitated. Furthermore, with the length of the tube, it will be possible to inject the injection material from outside the lens capsule 16 or from outside the eye. Further, by utilizing the surgery hole (with a small diameter) formed for the removal of the crystalline lens, the insertion of the balloon can be made by means of the tube without using the catheter. The tube 31 or 37 may be protruded from the capsule, and air remaining in the intraocular lens can efficiently be discharged out of the capsule. Furthermore, since the inlet and the outlet are formed in one tube, the space for attachment can be saved, the effect to the optical portion can be reduced, and the incision of the capsule can be made smaller. If a check valve 49 is provided to the balloon as the outlet, remaining air can effectively be discharged while injecting the injection material to the balloon. On the other hand, the reverse flow of air is effectively prevented. Once air is discharged, no air is permitted to enter into the intraocular lens.

If a gas permeable membrane is employed as the outlet, there will be no leakage of the injected material from the outlet, whereby it is possible to effectively discharge only air from the interior.

Figure 16B:
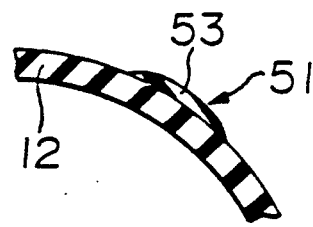

Further, as shown in FIGS. 16(a) and (b), it is possible to employ a thickened portion 51 i.e. a part of the balloon 12 is made to be thick. Such a thickened portion 51 may be formed integrally at the time of forming the balloon 12, as shown in FIG. 16(a), or a thickening member 53 is attached to the balloon 12 separately formed, as shown in FIG. 16(b). With such a balloon, a catheter is inserted to such a thickened portion 51 for injection of the injection material. The thickness of such a thickened portion 51 is usually from 1.05 to 1.20 times the wall thickness of the surrounding portion of the balloon 12, and the size is usually at most 4 mm in diameter.

Further, as such an inlet, it is possible to employ the above-mentioned check valve. The attaching position of such a thickened portion 51 and the check valve is the same as the case of the above-mentioned tubes 13 and 15.

Now, further embodiments for the inlet and outlet provided to the balloon of the invention will be described with reference to FIGS. 17(a)-(d).

Figure 17A:
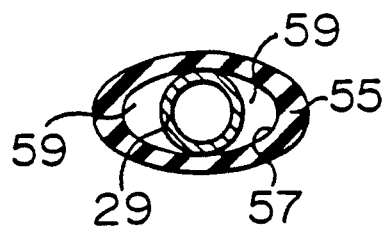

Firstly, FIG. 17(a) is a cross-sectional view of a tube 55 having an oval cross-sectional shape. This tube 55 has an inner hole 57 having an oval cross-sectional shape. The shape of the inner hole 57 is larger than the outer diameter of a catheter 29 for injecting a injection material, and designed to effectively hold such a catheter 29 in the inner hole 57.

Namely, for the insertion of a balloon provided with such a tube 55 into the lens capsule, the catheter is attached, and the insertion is conducted by means of the catheter. As shown in FIG. 17(a), when the catheter 29 is inserted in the inner hole 57 of the tube 55, the catheter 29 is effectively held by the inner surface of such an inner hole 57. At the same time, clearances 59, 59 will be formed as the outlet between the outer surface of the catheter 29 and the inner surface of the inner hole 57. Here, the shorter diameter portion of the oval of the tube 55 constitutes a supporting portion for holding the catheter 29 in the inner hole 57.

Figure 17B:
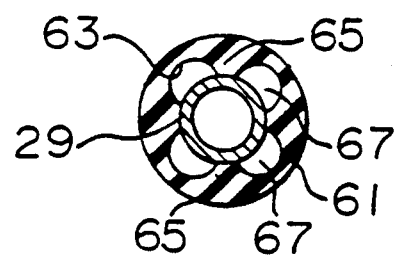

A tube 61 shown in FIG. 17(b) has a circular crosssectional shape, which has an inner hole 63 having a petal-like cross-sectional shape. As shown in the Figure, when a catheter 29 is inserted in such an inner hole 63, four supporting portions 65 projecting in the inner hole 63, hold the catheter, and at the same time, four clearances 67 are formed as the outlet between the inner surface of the inner hole 63 and the outer surface of the catheter 29.

Figure 17C:
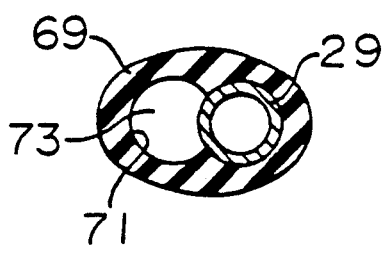

A tube 69 shown in FIG. 17(c) has an oval cross-sectional shape, which has an inner hole 71 having a letter-8 cross-sectional shape. As shown in the Figure, when a catheter 29 is inserted in one side of the letter-8 in such an inner hole 71, a clearance 73 is formed as the outlet on the other side of the letter-8. Here, the inner peripheral surface of one side of the letter-8 constitutes the supporting portion.

Figure 17D:
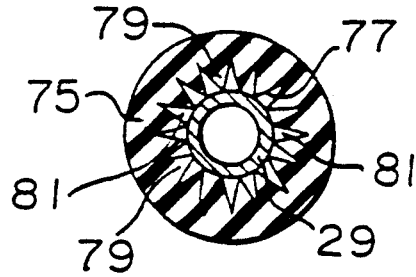

Further, a tube 75 shown in FIG. 17(d) has a circular cross sectional shape, which has an inner hole 77 having a star-like cross-sectional shape as shown in the Figure. When a catheter 29 is inserted into such an inner hole 77, a plurality of supporting portions 79 projecting in the inner hole 77, hold the catheter 29, and at the same time, a plurality of clearances 81 will be formed as the outlet between the inner surface of the inner hole 77 and the outer surface of the catheter 29.

These tubes 55, 61, 69 and 75 may be formed at the time of forming the balloon, or may be attached to the balloon independenly formed, like the above-mentioned tubes 13 and 15. The material and the attaching position may be the same as in the case of the tubes 13 and 15.

The operation for inserting the balloon provided with such a tube, is also the same as in the case of the balloon provided with other types of tubes as described above. With the balloon provided with such a tube, an injection material can be injected into the balloon by the catheter 29, and at the same time, air can readily be discharged through the clearances 59, 67, 73 or 81 formed by the insertion of the catheter 29.

Further, with the balloon provided with such a tube, substantially the same effects as obtainable by the balloon provided with the above described tube 31 or 37 can be obtained. Namely, formation of air bubbles during the injection of the injection material 14 can be minimized, and the catheter can be effectively held, whereby the insertion of the balloon into the lens capsule can be facilitated. Further, by utilizing the surgery hole (with a small diameter) formed for the removal of the crystalline lens, the balloon can be inserted by means of the tube without using the catheter. Further, the tube can be protruded outside the capsule, air remaining in the intraocular lens can efficiently be discharged out of the capsule. Furthermore, since the inlet and the outlet are formed in one tube, the space for attaching the tube can be saved, and the effect to the optical portion can be minimized, and the incision of the capsule can be minimized.

There is no particular restriction as to the shape of the inner hole of a tube of this type, so long as a catheter can be effectively held and a clearance as the outlet can be formed when the catheter is inserted therein.

In the foregoing, some of preferred embodiments of the present invention have been described. However, it should be understood that the present invention is by no means restricted to such specific embodiments.

For example, the configuration of the balloon described above has a hollow integral convex lenticular shape without projections along its circumference. In the present invention, such a balloon is acceptable so long as it is hollow and has a shape corresponding substantially to the posterior crystalline capsule.

Further, in order to facilitate the flow of air, it is possible to aspirate the air from the outlet by means of e.g. a pump.

Now, some Examples will be given wherein the balloon is provided with the inlet and the outlet.

EXAMPLE 4

Two silicone tubes (manufactured by Dow Corning, U.S.A.; outer diameter: 0.64 mm, inner diameter: 0.3 mm, cross section: substantially circular) were attached to a silicone balloon. From one of them, a 1% sodium hyaluronic acid solution was injected by means of a catheter, whereby air in the balloon was discharged from the other tube, and the interior of the balloon was completely filled with the aqueous sodium hyaluronic acid solution.

EXAMPLE 5

A silicone tube (manufactured by Dow Corning, U.S.A.; outer diameter: 1.22 mm, cross section: the same as shown in FIG. 17(b)) was attached to a silicone balloon. To this tube, a catheter of 2 french, and a polymerizable silicone was injected, whereby air in the balloon was discharged through the clearances between the tube and the catheter, and the interior of the balloon was filled with the polymerizable silicone. No remaining air bubbles were observed.

We claim:

1. A balloon for an intraocular lens capable of being inflated in a lens capsule to form an intraocular lens when a light transmitting injection material is injected into the balloon, which provides when inserted into the lens capsule a configuration corresponding substantially to the shape of the lens capsule, comprising:
    a unitary elastic hollow body made of an elastomer and having a convex lenticular shape without projections along its circumference, said hollow body having a wall thickness of from 0.001 to 0.1 mm at its light transmitting central portion and a diameter of from 6 to 13 mm;
    an inlet disposed on said hollow body providing an inlet for the injection of said injection material; and
    an outlet disposed on said hollow body for discharging gas from said hollow body while said injection material is being injected into said hollow body;
    wherein the inlet and the outlet are constituted by two pathways formed in one tube.

2. A balloon for an intraocular lens capable of being inflated in a lens capsule to form an intraocular lens when a light transmitting injection material is injected into the balloon which provides when inserted into the lens capsule a configuration corresponding substantially to the shape of the lens capsule, comprising:
    a unitary elastic hollow body made of an elastomer and having a convex lenticular shape without projections along its circumference, said hollow body having a wall thickness of from 0.001 to 0.1 mm at its light transmitting central portion and a diameter of from 6 to 13 mm;
    an inlet disposed on said hollow body providing an inlet for the injection of said injection material; and
    an outlet disposed on said hollow body for discharging gas from said hollow body while said injection material is being injected into said hollow body;
    wherein the hollow body has a tube having an inner diameter larger than the outer diameter of a catheter and provided therein with a supporting portion for holding the catheter which is inserted in the tube and held by the supporting portion, and said inlet is constituted by the catheter and said outlet is constituted by the space between the outer surface of the catheter and the inner wall of the tube.

3. A balloon for an intraocular lens capable of being inflated in a lens capsule to form an intraocular lens when a light transmitting injection material is injected into the balloon, which provides when inserted into the lens capsule a configuration corresponding substantially to the shape of the lens capsule, comprising:
    a unitary elastic hollow body made of an elastomer and having a convex lenticular shape without projections along its circumference, said hollow body having a wall thickness of from 0.001 to 0.1 mm at its light transmitting central portion and a diameter of from 6 to 13 mm;
    an inlet disposed on said hollow body providing an inlet for the injection of said injection material; and
    an outlet disposed on said hollow body for discharging gas from said hollow body;
    wherein the inlet and the outlet are constituted by two pathways formed in one tube.

4. A balloon for an intraocular lens capable of being inflated in a lens capsule to form an intraocular lens when a light transmitting injection material is injected into the balloon, which provides when inserted into the lens capsule a configuration corresponding substantially to the shape of the lens capsule, comprising:
    a unitary elastic hollow body made of an elastomer and having a convex lenticular shape without projections along its circumference, said hollow body having a wall thickness of from 0.001 to 0.1 mm at its light transmitting central portion and a diameter of from 6 to 13 mm;
    an inlet disposed on said hollow body providing an inlet for the injection of said injection material; and
    an outlet disposed on said hollow body for discharging gas from said hollow body;
    wherein the hollow body has a tube having an inner diameter larger than the outer diameter of a catheter and providing therein with a supporting portion for holding the catheter which is inserted in the tube and held by the supporting portion, and said inlet is constituted by the catheter and said outlet is constituted by the space between the outer surface of the catheter and the inner wall of the tube.

* * * * *